United States Patent [19]
Constantz

[11] Patent Number: 5,188,670
[45] Date of Patent: Feb. 23, 1993

[54] APPARATUS FOR HYDROXYAPATITE COATINGS OF SUBSTRATES

[75] Inventor: Brent Constantz, Scotts Valley, Calif.

[73] Assignee: Norian Corporation, Mountain View, Calif.

[21] Appl. No.: 686,525

[22] Filed: Apr. 17, 1991

Related U.S. Application Data

[63] Continuation-in-part of Ser. No. 504,941, Apr. 5, 1990.

[51] Int. Cl.$^5$ ............................................. B05C 3/109
[52] U.S. Cl. .................................... 118/667; 118/688; 118/602; 118/603; 118/416; 118/429; 118/503
[58] Field of Search ............... 118/667, 688, 602, 603, 118/416, 429, 612, 503; 137/93, 3, 5

[56] References Cited

U.S. PATENT DOCUMENTS

| | | | |
|---|---|---|---|
| 2,545,006 | 10/1944 | Ryan | 118/429 |
| 3,123,579 | 3/1964 | Lefevre | 118/429 |
| 3,658,676 | 4/1972 | DeVittrio et al. | 118/688 |
| 3,749,056 | 7/1973 | Primus et al. | 118/602 |
| 4,543,277 | 9/1985 | Giles | 118/416 |
| 4,794,018 | 12/1988 | Scheetz | 118/429 |
| 4,867,690 | 11/1990 | Fey et al. | 118/429 |
| 5,054,519 | 10/1991 | Berman | 118/429 |

FOREIGN PATENT DOCUMENTS 2406647 8/1975 Fed. Rep. of Germany ...... 118/429

Primary Examiner—W. Gary Jones
Assistant Examiner—Todd J. Burns
Attorney, Agent, or Firm—Bertram I. Rowland

[57] ABSTRACT

Methods, compositions and apparatus are provided for coating a substrate with a strongly adherent hydroxyapatite coating, which allows for ingrowth of natural bone and strong bonding between the coating and the substrate. The procedure provides for coating under conditions which form sticky particles which bind to the substrate to form a crystalline hydroxyapatite coating. The coating has particular application for prostheses, where porous areas of the prostheses are completely coated with a thin sturdy coating of hydroxyapatite.

The apparatus includes a coating trough in which the substrates are present and the reactive components added. The medium is recirculated in an outer circuit through a distribution tank solution preparation tank and coating trough. Means are provided for maintaining temperature and pH. The substrates are maintained in a line normal to the flow in the trough and can be rotated to ensure even coating.

4 Claims, 2 Drawing Sheets

APPARATUS FOR HYDROXYAPATITE COATINGS OF SUBSTRATES

CROSS-REFERENCE TO RELATED APPLICATIONS

This application is a continuation-in-part of application Ser. No. 504,941, filed Apr. 5, 1990.

INTRODUCTION

1. Technical Field

The field of this invention concerns mineralized coatings of prosthetic devices and equipment for producing such coatings.

2. Background

The use of prosthetic devices for treatment of bone injuries/illnesses is continuously expanding with an increasingly active and aging population. The use of bone replacements for bone fractures, removal of bone, or the use of supports for weakened bone requires that the artificial bone replacement form a strong joint or bond with natural bone to insure the integrity of the structure. Bone is able to grow into adjacent structure, particularly where the adjacent structures are porous and compatible with the bone. However, not only must the bone be able to grow into a porous structure, but there must be bonding in the form of a mechanical interlock in a form which allows for a strong bond between the natural ingrown bone and the prosthetic device.

The key requirement for bony fixation of prosthetic implants is that bone grow onto and/or into the implant's surface. A number of studies have shown that plasma-sprayed calcium phosphate coatings on Co-Cr and Ti-alloy implants foster more rapid bony apposition than the bare surfaced alloys alone. Because the alternative to attaining implant fixation is cementing the implant in with PMMA, which gives immediate fixation, there is a desire to create more rapid fixation via bone apposition, because during the ingrowth period there is movement between the implant and bone which leads to pain. Despite the pain, the cementless technique is used anyway because direct bony fixation is considered to be a better long term result than PMMA cements.

A number of techniques have been used to provide for a compatible surface to an otherwise incompatible but structurally acceptable prostheses. Metals have been coated with calcium phosphate ceramics by plasma spraying, ion implantation, and the like. Metal, fibers or beaded porous ingrowth surfaces have been coated by the above techniques. However, the coatings are frequently thick and brittle, have shadows where no coating has occurred, clog the pores within the porous coating and are subject to fracture. Furthermore, these techniques do not lend themselves readily to the inclusion of growth factors which may be useful in encouraging bone ingrowth and maintenance.

It would therefore be of interest to be able to develop coatings which will be compatible with bone ingrowth, provide strong bonding between the natural bone and the supporting unit and allow for binding various endogenous and exogenous factors which encourage bone growth and maintenance.

3. Relevant Literature

U.S. Pat. No. 4,693,986 provides a description of the state of the art concerning apatite products as bone substitutes. Okazakai, J., et al., Biomedical Materials Research (1982), 16:851–860; Okazakai, J., et al., Caries Res. (1984), 18:499–504; and Okazakai, J., et al., J. Dent. Res. (1981), 60:845–849, described the presentation of hydroxyapatite needle-like crystals. Calcium phosphate fibers are described in a number of Japanese patents including: JP57/117621; JP53/111000; JP53/110999; JP61/201019; and JP58/054023. German Publication No. DE 33 39 996 describes calcium carbonate needles and particles. U.S. Pat. No. 3,959,192 describes calcium carbonate particle fillers. Napper and Smythe, J. Dent. Res. (1966), 45:1775–1783, describe the preparation of hydroxyapatite crystals using calcium acetate. For a review of calcium phosphate ceramics as hard tissue prostheses, see Jarcho, Clinical Orthopedics and Related Research (1981), 157:259–278. Discussion of octacalcium phosphate may be found in LeGeros et al., Scanning Electron Microscopy (1984) 4:1771–1777 and references cited therein.

SUMMARY OF THE INVENTION

Novel methods and compositions are provided relating to hydroxyapatite, particularly as coatings on a porous substrate. The method involves combining a soluble source of calcium with a soluble source of phosphate under conditions of controlled nucleation and modulated crystal growth to form an hydroxyapatite coating on a substrate with a crystalline whiskered surface. The stable substantially uniform coatings are obtained on porous structures which allow for bone ingrowth.

Apparatus is provided for controlling uniform growth of a plurality of substrates, employing a coating chamber, recirculating means and ports for introducing reactants in a predetermined order.

DESCRIPTION OF THE SPECIFIC EMBODIMENTS

Figure 1:
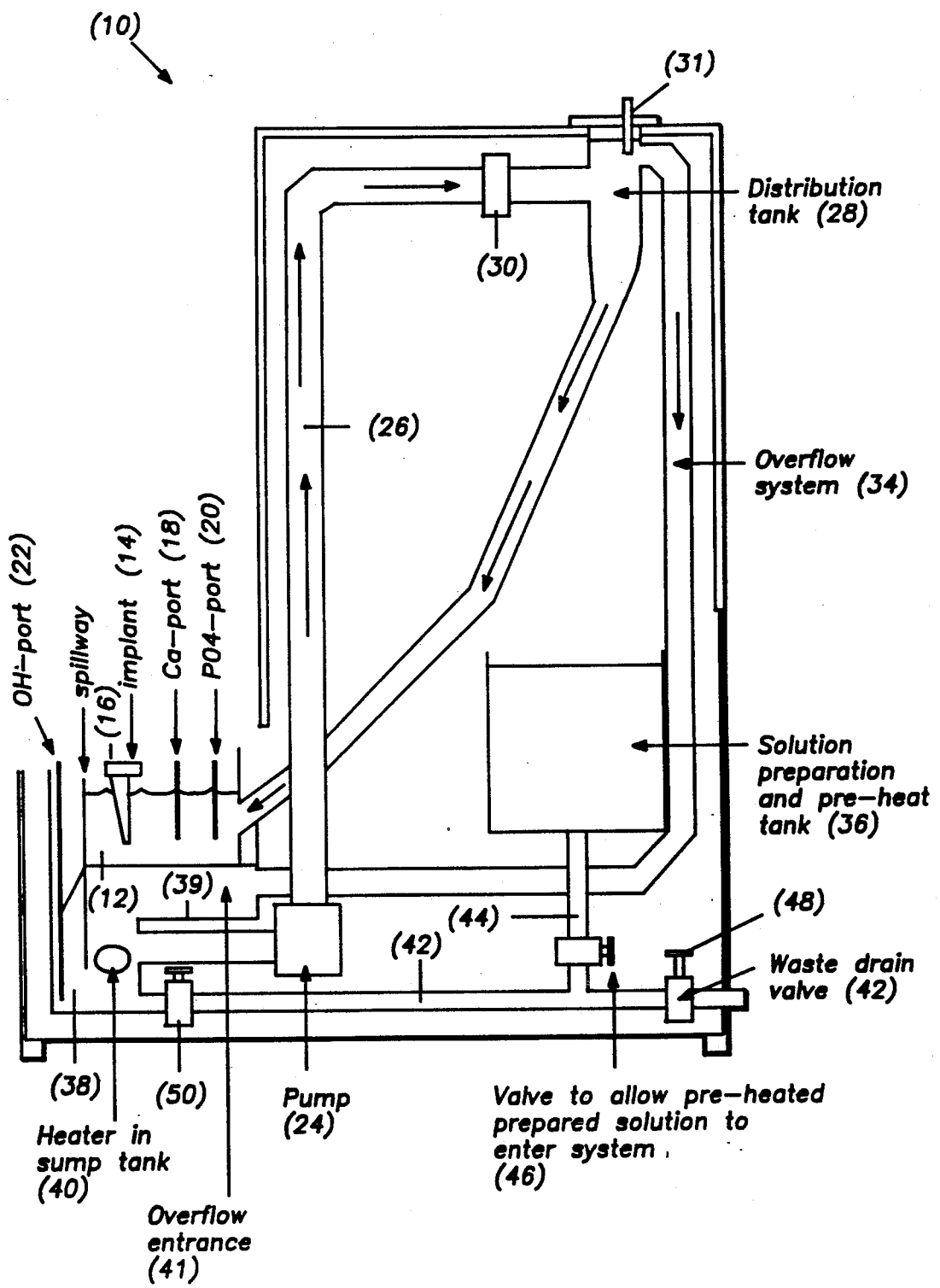
FIG. 1 is a diagrammatic elevational view of an apparatus according to the subject invention.

Methods, compositions and devices are provided for producing hydroxyapatite, particularly as coatings on substrates, e.g., prosthetic devices, which interact with bone or provide for bone ingrowth. The coatings are produced in a process which provides for a strong adherent uniform thin coating of hydroxyapatite on a substrate surface, where the coating has long needles or whiskers, which appear to induce bone ingrowth and strong bonding between natural bone and the coating via bone ingrowth and apposition on a pore comprising implant.

The coatings are found to have a high $Ca_{10}(PO_4)_6(OH)_2$ surface area because of fibrous hydroxyapatite crystals $Ca_{10}(PO_4)_6(OH)_2$. The surface area will generally range from about 1–25 $m^2/cm^2$ of area. The coatings may be as thin as about 2 $\mu m$ ($\mu m$=microns), preferably being at least about 5 $\mu m$, and more preferably at least about 10 $\mu m$, and may range to 40 $\mu m$ thick or greater, depending upon need. Usually, a relatively thin coating will be employed to avoid thick brittle ceramic interfaces between the substrate and the ductile bone.

The hydroxyapatite composition may be modified in a variety of ways by the introduction of other ions, as required. Other ions include fluoride, carbonate, sodium, chloride, hydrogen ions, e.g., $HPO_4$, $HCO_3$, etc., and the like. Usually fewer than about 50%, more usually fewer than about 20% of the total number of phosphate and hydroxide anions and up to 50% of calcium cation will be substituted with other ions. These substitutions will influence the in vivo dissolution behavior of the coating which may be resorbable or unresorbable.

The single crystals or whiskers which are produced by the subject method will generally range from about 0.01 microns to 20 microns in diameter and about 1 micron to 40 microns in length. The composition will usually be substantially homogeneous ($\geqq 95\%$), mineralogically pure (same crystal structure), ($\geqq 90\%$) and substantially homogeneous morphologically, generally varying by no more than $\pm 20\%$ from the average of each dimension.

The hydroxyapatite (HAP) has a net positive charge at physiologic pH which attracts negatively charged proteins, such as collagen or other exogenous or endogenous proteins, which may serve as growth factors, chemoattractants, and the like. Thus, the coating may provide for the presence of such products on the surface of the hydroxyapatite or its analog or as part of the structure of the hydroxyapatite. The exceptionally high surface of this coating presents orders of magnitude more binding surface than the uncoated implant or the conventional calcium phosphate coatings.

The coatings may be applied to solid surfaces, porous surfaces, etched surfaces, or any other type of surface. Because the coating is applied in a liquid medium which is able to penetrate channels, pores, indentations and other structural features, a uniform coating can be obtained which can coat substantially the entire surface, without leaving exposed areas. The subject process finds particular application with devices involving fine bead layers, where the beads will be two or more layers, requiring that at least about two layers of the beads be penetrated and coated with the hydroxyapatite or its analog. Thus, penetrations are achieved in a porous substrate, such as is used in prothesis devices, of at least about 0.5 mm, more usually at least about 1 mm.

The method involves providing for the formation of small sticky hydroxyapatite particles as a colloidal suspension in proximity to the substrate to be coated. The particles are directed by a stream at a velocity which results in impact of the particles onto the surface of the substrate and binding of the particles to the surface. Further increase in the thickness of the coating may result from particle and/or soluble ions by accretion, probably particle. The surface, under the conditions of the coating process, results in a whiskered crystal surface of hydroxyapatite.

The substrates may be coated in a single container where the medium is agitated by stirring and reactants and reagents continuously added to maintain the reactants in the presence of the substrate in the proper concentration range and the conditions at the appropriate levels.

The method in a non-circulating mode involves applying at least two layers, a first layer of very small crystals achieved by providing conditions which result in a high density of heterogeneous nucleation sites, so that there is a large number of hydroxyapatite nucleation sites on the substrate. This is followed by at least one additional coating under conditions which provide for a lower level of nucleation modulated crystal growth, so as to produce substantially larger crystals. Desirably, one or more additional coatings are provided, where the conditions are the same or at even lower levels of nucleation than the second coating to produce larger size crystals as compared to the second coating. Usually, there will be not more than five coatings, preferably not more than about three coatings.

The first layer will generally be of a thickness in a range of about 0.01 micron to 20 microns, with crystal size in length in a range of about 0.01 microns to 10 microns. The second coating will generally be of a thickness in a range of about 1 micron to 40 microns, with crystals of a size in length in the range of about 0.01 microns to 20 microns. The third and successive coatings will generally range as to each layer of a thickness in a range of about 1 micron to 40 microns, preferably about 5 microns to 10 microns, having crystals of a diameter of about 0.1 to 2 microns, and a length of about 1 to 10 microns, preferably about 0.1 to 1 micron in diameter, and a length of about 2 microns to 7 microns. The total thickness of the second and succeeding layers will generally be in the range of about 5 microns to 20 microns.

The various layers can be achieved, by varying the concentration of the reactants, the pH, temperature, manner of combining the reactants in the reactor, nature of the liquid flow, and the like. Preferably, the reactants nd substrate will move in relation to one another, so that the substrate is continuously encountering a specific reaction mixture. Conveniently, the reaction mixture may be streamed past the substrate, using laminar or turbulent flow, preferably turbulent flow, by using a mixer, where the portion of the substrate to be coated is positioned at a site displaced from the center of the reactor and the reaction mixture continuously agitated with a stream flowing around the walls or the like. The specific conditions for the reaction mixture are determined by the flow conditions determined by reactant concentration, geometry of combination, fluid flow regime, vessel geometry, and the like.

Before coating is started, the substrate may be cleaned or treated to remove any surface contaminants or other treatment to promote good adhesion of the coating. Various methods for cleaning may be employed. Before the coating, the substrate may be rinsed with a degreaser, e.g., acetone, isopropanol, freon, etc. and then rinsed with an appropriate rinsing solution, e.g., deionized water. Surface treatments available are acid etchings, ion beam etchings, etc.

The reaction mixture is prepared by bringing together at an elevated temperature and at a mildly acidic to mildly basic pH, a water soluble calcium source and a water soluble phosphate source. During the addition of the calcium and phosphate sources, the pH is maintained by the addition of an appropriate acidic or alkaline medium particularly alkaline medium, e.g. ammonium hydroxide. Depending upon the particular coating involved, the solutions which supply the calcium and phosphate sources will vary in concentration, so as to vary the degree in rate of nucleation, an crystal growth modulation.

While the two reactants may be added simultaneously at an adjacent site, preferably, the calcium source will be added at a site more proximal to the substrate than the phosphate source. Thus, the calcium will be introduced into a solution in which the phosphate concentration has been replenished and these combined solutions will then directly encounter the substrate after a specific amount of mixing which is adjusted in accordance with the nature of the desired coating. Usually, the time from which the calcium source and the replenished phosphate solution meet to the time for encountering the substrate will be less than about 1 sec., more usually less than about 10 msec. With continuous recycling, the final volume of the solution will generally be from about 1 to 30 times greater than the volume of the two solutions added, usually about 1 to 2 times greater.

The reactant solutions and the parent solution may be preheated or used at ambient temperature, generally being added at a temperature in a range of at least 20° C. to not more than about 90° C. The reaction may be maintained at a temperature in the range of about 60°-90° C., preferably in the range of about 70°-85° C. The pH will be maintained in the range of about 5-8.5, more usually about 6-8, preferably about 6.5-7.5. The pH of the individual reactants and the parent solution may be individually adjusted to provide for specific crystal nucleation and crystal growth conditions.

The molar ratio of the solutions will generally have the calcium source at a molar ratio of 1-2:1 to the phosphate source, more usually of about 1.5-2:1 to the phosphate source. The molarity of the most dilute concentration of the calcium source will generally be in the range of about 0.05 to 5M, more usually about 0.1 to 2.0M. The phosphate source will generally be from about 0.01 to 1.0M preferably about 0.05 to 0.5M. The more concentrated solution will generally range in concentration from about 2 to 10 times the lesser or least concentrated, more usually from about 2 to 8 times. The first reaction mixture solution, which provides for the high nucleation, will generally be at a concentration at least about 1.5 times the most dilute reaction mixture solution employed, more usually at least about 3 times, and not more than about 10 times, usually not more than about 7 times the most dilute reaction mixture solution. Particularly preferred is a series where the various solutions are about 5 times, then about 3 times more concentrated than the last and most dilute solution. The calcium and phosphate source will be added to provide a substantially stoichiometric ratio of the components of hydroxyapatite.

The calcium source may use any convenient counterion, depending on the purpose of the final product. Where the final product is to be introduced into a host, desirably only physiologically acceptable counterions will be employed. For the calcium salt, various organic and inorganic anions providing a water soluble source may be employed, such as acetate, succinate, nitrate, chloride, malonate, maleate tartrate, fumarate or other chelating anion. Of particular interest are carboxylates of 2 to 6, usually 2 to 4 carbon atoms. For phosphate, alkali metal or ammonium salts may be used, particularly sodium or ammonium. The choice of counterions and mixtures thereof will be determined to some degree on the interaction of the counterions, so as to avoid any precipitation or involvement of the counterions in the crystal structure.

The time for each coating will vary depending upon the particular substrate, the concentrations and conditions employed, and the like. Generally, each coating will take at least about 5 minutes, more usually at least about 30 minutes, and not more than about 12 hours, more usually not more than above 6 hours. Preferably, the time for the coatings are varied in a range from about 1 to 6 hours.

The substrates are introduced into the solution, where the substrate will preferably be down stream from the more proximal calcium source. Thus the phosphate source will preferably move downstream to combine with the calcium stream before encountering the substrate to be coated. Those areas not to be coated may be protected by a convenient protective coating or the coating may be removed from those areas which are not protected after completion of the process. Variations in concentration of the reactants can be achieved by either using more dilute solutions for addition of the reactants or by using different volumes and concentrations for the initial parent solution in which the substrate is immersed. Where the reactants are continuously added to the reaction mixture, after completion of the addition, the reaction may be allowed to continue, the additional time usually requiring from about 50 to 400%, usually from about 75% to 200%, of the total time for each individual layer formation.

After each coating the surface may be prepared by thorough cleaning to remove any surface contaminants for the next coating. Various methods for cleaning the substrate may be employed. After each coating, the samples may be removed and, carefully rinsed with an appropriate rinsing solution, e.g. deionized water. If desired, the sample may be dried and inspected by employing a volatile water miscible organic solvent, e.g., acetone, rinsing with the organic solvent, followed by air drying. After each individual coating, desirably the substrates are turned 180° to insure that the substrates are coated uniformly. When the coating has been completed, the samples are then inspected to insure uniformity, adhesion to the substrate, surface area enhancement, and for any other characteristic which may be appropriate.

Where a circulating system is employed so that a stream is continuously entering and exiting the coating reactor, a single coating step is required, where the coating process is continued until the desired thickness is obtained; generally in less than about 120 min, usually at least about 10 min. The pH is maintained at about 6.8 to 8.0, preferably about 7.4. The temperature at the substrate will usually be in the range of about 70° to 90° C., preferably about 80° C. Preheating of reagents may be advantageous.

The solution will generally be in the range of about 1 to 2M ammonium acetate, increasing with time due to evaporation. The concentration of the calcium source will generally be in the range of about 0.1 to 0.8M, preferably about 0.3 to 0.6M, more preferably about 0.5M, while the phosphate source will range from about 0.06 to 0.5M, preferably about 0.2 to 0.4M, more preferably about 0.3M. Core ammonium hydroxide is added to maintain the pH. The water used will desirably be low in carbonate, such as deionized water. Usually, the coating will not exceed 20μ, more usually not exceed 10μ in thickness.

The subject coatings may be combined with a wide variety of materials, such as collagen, bone growth factors, such as TGF-β, bone morphogenetic factor, combinations thereof, or the like. The growth factors may serve to enhance the growth of osteoblasts, while the growth factors and collagen may enlist bony ingrowth. These factors may be included in the reaction mixture or in a storage solution. Generally, the growth factors will be present in the solution in from about 1 μg/ml to 1 mg/ml. The coated devices can be shipped in aqueous media, where one or more factors may be present in the solution in which the coating is immersed Alternatively, these factors may be freeze-dried onto the coated substrate to which they bind and then the device shipped dehydrated.

Various implant devices, for example, the femoral component of a total hip arthroplasty may be used where the devices may be composed of a wide variety of materials, particularly metals or hardened plastics, e.g. Co-Cr, Ti alloy steel, polyethylene, carbon fibre reinforced resins etc.

For carrying out a large number samples in a continuous carefully controlled and reproducible manner, one can provide for one or a plurality of coating troughs, each of which can accommodate a plurality of samples which will be subjected to a substantially uniform composition simultaneously. The apparatus will include ports for introducing a source of calcium, phosphate, and neutralizing base in a predetermined order in relation to the positioning of the substrates to be coated, with the neutralizing base downstream from the substrate. By providing for continuous circulation, pH and temperature monitoring, the coating solution may be maintained substantially constant as to composition and conditions The substrates to be coated may be mounted to allow for rotation or rocking of the substrates, so that they may be evenly coated on all sides.

It is sometimes desirable to coat only specific portions of the implant. Mask devices fabricated from a variety of materials can be used to mask implants. Among the most common method is making a reusable mold with RTV silicone rubber because it is highly flexible and readily available. A single component material is desirable. Another process is dipping the implant into a material such as Plastisol to form a thin (plastic or rubber) mask. The mask can either be reused or disposed of after peeling off. A third possibility is acrylic tape. These materials must withstand the solution pH, temperature, and chemical compatibility to be used.

For further understanding of the subject apparatus, FIG. 1 is provided. The device 10 has a trough 12 in which are placed the substrates 14 supported by a holder 16. Only one trough is shown, but the device may accommodate five or more troughs. The trough includes a calcium inlet port 18, a phosphate inlet port 20 and an hydroxide port 22. In this manner, the circulating solution is replenished with calcium and phosphate and the pH controlled downstream from the reactant ports and substrate Circulation of the medium is provided by suction pump 24 which removes solution from trough 12 and cycles the solution through conduit 26 to distribution tank 28. The distribution tank is used to recycle the solution to a plurality of troughs, only one being shown. A filter 30 may be included in conduit 26 to remove small particulate matter which may form during the reaction. A pH probe 31 is provided in the distribution tank 28 to monitor any changes in the pH and to control the rate at which hydroxide is added to the recirculating solution from hydroxide port 22. The distribution tank 28 divides the solution into two parts, a first portion which is continuously fed back to the trough 12 through conduit 32 and a second portion for overflow from distribution tank 28 through conduit 34 to the sump 38.

A solution preparation tank 36 is provided for preparation of the initial medium for filling the trough 12 and heating the medium to the described temperature. A sump 38 is equipped with heater 40 for maintaining the temperature. The sump 38 is divided from the overflow entrance 41 by divider 39. Optionally, a heater may be maintained in solution preparation tank 36, in addition to heater 40 for heating the medium prior to filling the trough.

A drain pipe 42 is provided for draining from sump 38 as well as from solution preparation tank 36 by being connected to solution preparation tank 36 through conduit 44. Valve 46 is provided for controlling the flow through conduit 44 and valve 48 controls flow through drain conduit 42. Valve 50 controls the flow from sump 38.

Figure 2:
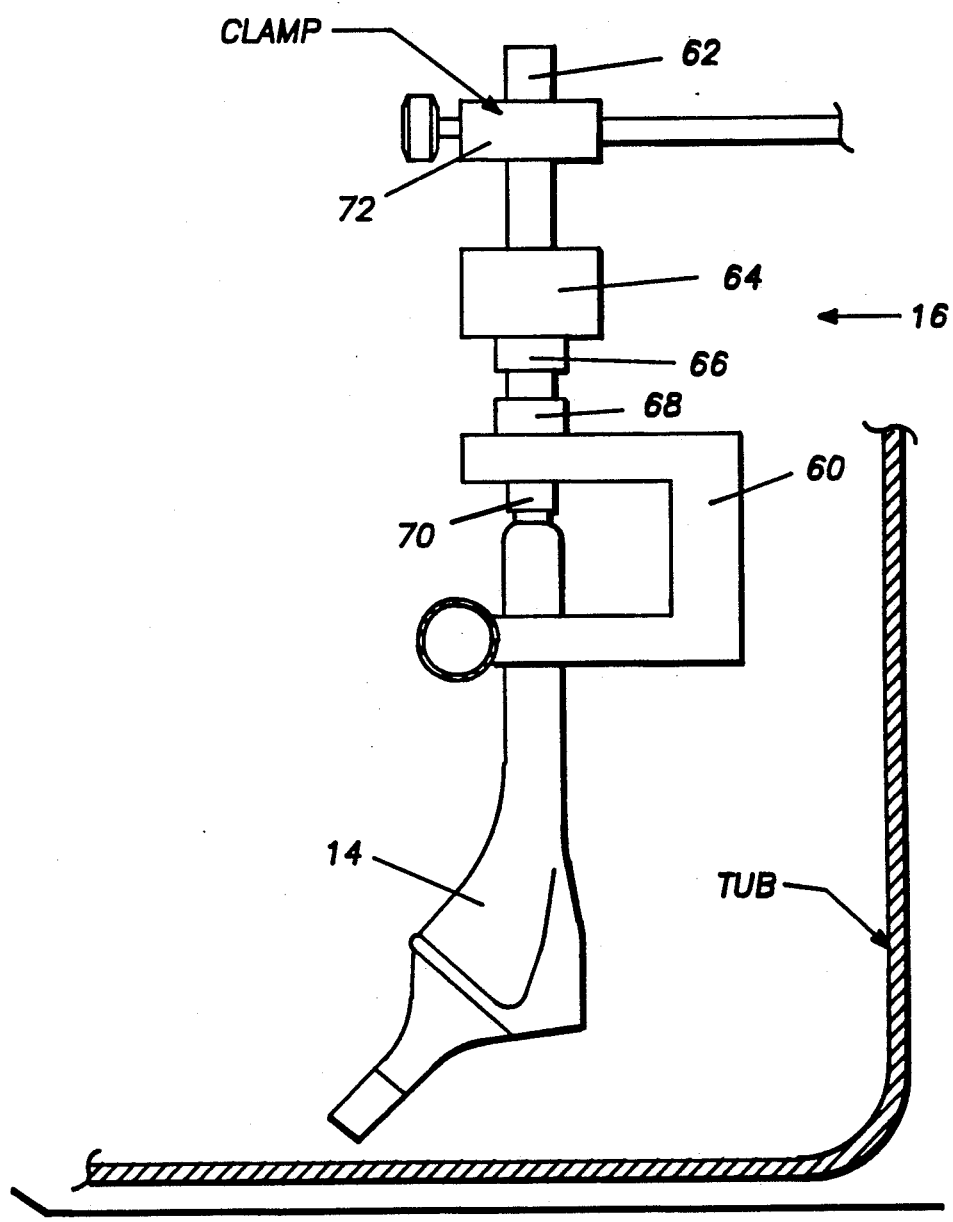
FIG. 2 is a diagrammatic side elevational view of the substrate holder and substrate.

A holder 16 is provided for supporting the substrate 14 in the coating medium. The holder 16 has a clamp body 60 (FIG. 2). Rod 62 extends downwardly through collar 64 and knurled lock knobs 66 and 68, terminating in housing 70 which holds substrate 14. Rod 64 may be adjusted for height by means of clamp 72. The entire holder may be mounted on a rocking device or rotating device which allows for individual movement, or each holder 16 may be individually mounted to provide the appropriate movement pattern.

Desirably a rocking movement is employed, where the holders are mounted so as to pivot around a central point up to about 30° from a line normal to the flow direction.

An exemplary subject apparatus may have a trough volume of 22 liters, with a maximum capability of feed of the different components of up to about 2 liters. The solution preparation tank in conjunction with the trough would have a capacity of about 400 Liters. The capacity of the distribution tank would be about 50 liters. The 100-recirculation pump would have a capacity of about 130 gph. The filter, if present, would remove particles in the range of about 10 $\mu$m to 350 $\mu$m.

The following examples are offered by way of illustration and not be way of limitation.

EXPERIMENTAL

Protocol

Carefully cleaned samples are introduced into a 3L insulated beaker comprising 25.05 g ammonium acetate in 250 ml of deionized water (dH$_2$O). The samples are downstream from a calcium acetate addition port and a rotating motorized stir propeller is centered and rotated at 60 rpm. The beaker is placed on a 9 inch heat/stir plate and the heat turned on to 8.0. The beaker is covered with a protective film to reduce evaporative heat loss. When the ammonium acetate solution has been heated to 75° C., the pH meter is turned on and the pH monitored, so that the solution is maintained at 80° C. and pH 7.4. Addition is then begun of the reactants at a rate to provide the desired stoichiometric ratio, where a solution 0.5M in calcium acetate and a second solution 0.3M in ammonium phosphate monobasic is continuously added, while maintaining the pH by the addition of concentrated ammonium hydroxide. The addition is carried out over a period of two hours, at which time stirring and heating is then continued for an additional two hours to provide a total period of about four hours.

The sample substrate may then be removed, washed, dried by washing with acetone and allowed to air dry, if the substrate is to be inspected between coatings.

The above procedure is repeated, except the solutions employed have 60% of the original concentration. A third coating may then be employed where the reactant solutions have 20% of the original concentration.

When the coatings are finished, the coatings are inspected by rubbing with a bare finger or glove to determine whether the coating comes off and by placing a piece of VWR lab tape on the surface and pulling the tape off. If in either case, significant bare metal is exposed, the coating may be removed and the process repeated.

The general procedure described above was followed with six Vitallium porous-implant rods from Howmedica Inc. (Rutherford, N.J.) The system was set up as described and the coating begun when the temperature reached 80.0° C. and the solution was at pH 7.4. The run required four hours during which time the temperature varied from about 79° to 84° C. and the pH from about 7.39 to 7.43. About 160 ml of conc. ammonium hydroxide was used to maintain the pH. After about 20 min., polyethylene balls were added to minimize evaporation. The rods were turned after about 30 min. and one hour, while the rods were moved in a clockwise direction at about 95 min. and the beaker moved to maintain the spatial relationship between the rods and the reagent sources. Addition of reagents was completed at about 115 min.

Devices comprising Co-Cr beaded rod (Howmedica PCA surface) were prepared as described above for transmetaphyseal femur implants, with a 1 mm radial gap in fifteen dogs.

The protocol provides for the evaluation for safety and effectiveness of a bioceramic coating applied to a Vitallium porous-coated implant. Further, it also tests the ability of the coating to bridge a clinically relevant 1 mm bone-implant gap. The study uses the dog as an animal model. The non-weight bearing model has implants placed across each femoral condyle with a 1 mm gap maintained throughout the cancellous region of the condyle. One femur has the coated implant inserted. The contralateral femur has the uncoated plug implanted and serves as a control. This model allows the mechanical and histologic evaluation of the bone-implant interface.

The purpose of the non-weight bearing study is to show the effectiveness of the applied bioceramic coating to the implant surface. Effectiveness is evidenced by a significantly increased push-out strength as compared to the non-coated implant. Additionally, the safety of the coating on the non-weight bearing implant and the osteoconductive ability of the bioceramic coating can be assessed by histopathologic evaluation of the implant site.

Experimental Design

A porous-coated Vitallium plug is surgically implanted transcondylarly into the distal femur of 15 adult dogs. The plugs are placed bilaterally, one femur has a plug coated with the bioceramic material while the contralateral femur has a non-bioceramic coated plug implanted. The bone-implant interface is evaluated mechanically to quantify the shear force required to initially dislodge the implant. On representative paired specimens, undecalcified histology is performed to determine the mode of interface failure and skeletal reaction to the bioceramic coating.

The 15 dogs are divided into 3 groups. Groups I, II, and III each has 5 subjects. The respective sacrifice times following implantation of the coated and uncoated plugs are 3, 6, and 12 weeks.

Experimental Subjects

Skeletally mature, heartworm-free dogs are used as experimental subjects. The animals are examined for any evidence of disease. Skeletal maturity and the absence of previous or current skeletal pathology is confirmed radiographically. The minimum body weight is approximately 20 kilograms.

The breed and sex of the dogs used is dependent on laboratory animal availability. Where possible, purpose-bred subjects of known ages are used. If purpose-bred animals are used, the dogs do not vary by more than one year in ages.

Animal Housing

The subjects are conditioned for an appropriate period of time. Following quarantine, the animals are maintained in runs, either individually or in pairs, depending on the cage size. Animal housing conditions conform with the applicable laws and regulations relating to laboratory animals, i.e., Animal Welfare Act, Public Law 89-544 as amended in Public Law 99-198, Federal Register 52:61, United States Department of Agriculture—Animal and Plant Health Inspection Service (USDS-APHIS), 1985 and Public Health Service Policy on Humane Care of Laboratory Animals, Office for Protection Against Research Risks/National Institutes of Health (OPRR/NIH), Sep. 1986.

Implant Description

The porous-coated Vitallium implants have two different surface conditions. These are the bioceramic coated and uncoated surfaces. The dimensions of the implants are approximately 6.4 mm in diameter and either 25 mm or 30 mm in length. Both ends are cut straight to allow attachment of an 8.4 mm diameter by 3 mm thick teflon washer. Two washers, one on each end of the plug are attached.

All of the implants are supplied by Howmedica. They are sterilized in individual packages with a pair of teflon washers included.

Surgical Technique

The surgical implantation technique is identical for both rearlimbs. All surgeries are done under strict asepsis. Peri-operative antibiotics and pre-anesthetic medication is dosed at he discretion of the surgeon. Anesthesia is induced with an ultra-short acting barbiturate followed by endotracheal intubation. The subject is maintained with a balanced mixture of oxygen and an inhalatory anesthetic agent.

The surgical approach is as follows. A curved, lateral skin incision is made from the distal one-third of the femur to the level of the tibial plateau. The skin is bluntly dissected and retracted to allow a lateral parapatellar approach into the stifle joint. An incision is made parallel to the lateral border of the patella and patellar ligament. This extends from the lateral side of the fascia lata along the cranial border of the biceps femoris and into the lateral fascia of the stifle joint.

The biceps femoris and attached lateral fascia are retracted allowing an incision into the joint capsule. The joint is extended and the patella luxated medially exposing the femoral condyles.

The desired point of drilling is from the middle of the lateral to medial condyles, midway between the fabella and the most cranial part of the trochlear ridge. The lateral fabella are identified with a sterile needle to assist in determining the point of drilling. A pilot drill hole is placed once the alignment has been verified. The depth across the condyles is measured with a depth gauge in order to determine if the 25 mm or 30 mm long implant should be used. After the desired implant is chosen the hole is sequentially enlarged until an 8.4 mm drill hole is achieved. The periosteum around the lateral drill hole is reflected to prevent being pulled in during insertion of the implant. The drill hole is flushed from the lateral to medial direction with sterile saline.

The plug and lateral washer assembly is placed into the hole from the lateral side. The medial washer is then attached to the opposite end of the plug. An equal amount of the implant should protrude from the lateral and medial border of the condyles. Routine closure of the joint is accomplished in three or four layers using appropriate suture material.

The distribution of implants for each dog in the three groups is described in the following Table reporting the results:

Post-Operative Period

If possible, following the completion of surgery, with the animal still anesthetized, post-operative radiographs are made. Two views are taken, the lateral to medial and the craniocaudal view. Care is taken to assure the views are parallel to the plane of the implant. At this time, the anesthetic gas is turned off and oxygen flow maintained for five minutes. The subject is returned to the prep room after the radiographs are taken. A modified Robert-Jones bandage is applied to each hindlimb. The endotracheal tube is pulled once the subject displays a swallowing reflex. Following removal of the endotracheal tube, the dog is moved to a cage to recover. Post-operative analgesics are given if the animal displays any signs of distress or discomfort.

The day after surgery, if the animal is able to walk, it is returned to the housing quarters. The bandages are checked daily. After 2-5 days, the bandages are removed. New bandages may be put on, as appropriate. Skin sutures, if present are removed 10-14 days post-op. All animals are examined daily for signs of pain or infection. Appropriate measures are taken if either occurs.

The subjects are housed for either 3, 6, or 12 weeks after implantation. During this time, normal activity is allowed. Radiographs are made at the time of sacrifice. As before, two views, the lateral to medial and the craniocaudal, are taken. The positioning is the same as the previous films.

Fluorochrome Bone Labels

Oxytetracycline is given at a single dose of 30-35 mg/kg intravenously. This is generally done 3 days prior to sacrifice.

Euthanasia

The subjects are euthanatized at the end of the study in a humane manner according to the guidelines set forth by the AVMA Panel on Euthanasia (JAVMA, Jan. 1986).

Specimen Collection and Handling

Immediately following sacrifice, the rearlimbs are disarticulated at the coxofemoral and patellofemoral joints. All soft tissues are removed. Popliteal and inguinal lymph nodes are isolated and fixed in formalin for later evaluation. The paired femurs are labeled and frozen.

For shipping for evaluation, the specimens are frozen in dry ice.

Mechanical Testing and Histology

To mechanically evaluate the bone-implant interface strength, a push-out test is conducted. Each femoral condyle is sectioned through the lateral and medial cortical wall of each condyle on the inner surfaces of the teflon washers, orthogonal to the plane of the implant, with a low deformation wire saw. The direction of applied force is from medial to lateral, opposite to the direction of insertion. The cross-head speed of the testing machine is 0.5 mm per minute. The testing is stopped when the force to push-out the implant begins to decline.

The tested specimens are sequentially dehydrated in increasing concentrations of ethanol. They are embedded in methacrylate, sectioned either sagittal or orthogonal to the implant, and microradiographs taken. This is followed by grinding to a desired thickness and differential staining. The prepared sections are evaluated with light and ultra-violet microscopy to determine the mode of bone-implant failure and to assess the skeletal reaction to the uncoated and coated surfaces.

The following table provides the results of the test with the porous-coated Vitalluim plug coated in accordance with the subject invention as described above.

| ANIMAL STUDY | | | |
|---|---|---|---|
| Animal Number | Group (week) | Coated (MPa) | Uncoated (MPa) |
| 1201 | 3 | 0.82 | 0.21 |
| 1203 | 3 | 0.60 | 0.24 |
| 1774 | 3 | 1.19 | 0.39 |
| 1769 | 3 | 0.10 | 0.03 |
| 1771 | 3 | 0.55 | 0.14 |
| mean ± sd | | 0.65 ± 0.36 | 0.20 ± 0.12 |
| 1208 | 6 | 1.75 | 0.35 |
| 1205 | 6 | 0.72 | 0.51 |
| 1210 | 6 | 0.79 | 0.20 |
| 1537 | 6 | 1.90 | 0.25 |
| mean ± sd | | 1.29 ± 0.61 | 0.33 ± 0.13 |
| 1206 | 12 | 3.11 | 0.83 |
| 1200 | 12 | 3.16 | 0.40 |
| 1278 | 12 | 2.61 | 0.31 |
| 1202 | 12 | 1.31 | 0.65 |
| 1535 | 12 | 3.28 | 0.87 |
| mean ± sd | | 2.69 ± 0.73 | 0.61 ± 0.22 |
| STATISTICAL ANALYSIS | | | |
| Student's Paired T-Test | | | |
| 3 week group n = 5 | | $0.05 < p < 0.02$ | |
| 6 week group n = 4 | | $0.10 < p < 0.05$ | |
| 12 week group n = 5 | | $0.01 < p < 0.001$ | |

Histomorphometry also shows that the subject coating results in the gap being filled and, statistically decreases the time in which the gap is filled. The subject coatings are biomechanically competent.

It is evident from the above results, that the subject method provides for strongly adherent coatings, which do not fracture readily and promote ingrowth of natural bone. The method provides for the coating of all surfaces, even hidden surfaces, which is a distinct advantage as compared to other techniques for coating porous portions of prostheses. In addition, the surfaces allow for binding of a wide variety of proteins, and can be shipped in a state which maintains in solution various additives, which may aid in the interaction with native bone and the prosthesis. The coating procedure is substantially reproducible, allowing for uniformity and homogeneity of the coating composition. Bonding to the substrate is found to be strong, so that the coated substrate may be subjected to reasonable abrasion and handling without affecting the coating. The subject calcium phosphate coating fosters rapid bony ingowth due to its high peptide-binding surface area which stimulates osteogenesis. The subject compositions provide for a bone growth factor delivery surface coating. The subject apparatus allows for the simultaneous controlled reproductable coating of a plurality of substrates.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An apparatus for preparing a strong adhering hydroxyapatite coating to a substrate, said apparatus comprising:
   a coating trough;
   a distribution tank;
   a solution preparation tank;
   means for circulating a coating medium in a continuous manner in a circuit from said coating trough to said distribution tank to said coating trough;
   heating and pH control means for controlling the temperature and pH of said circulating medium;
   means for transferring solutions from said solution preparation tank to said circulating means;
   individual source means for adding calcium, phosphate, and neutralizing base, wherein said calcium and phosphate sources feed into said coating trough, where in the direction of flow in relation to said substrate, said calcium source is proximal to said substrate while said phosphate source and neutralizing base source are respectively more distal from said substrate, whereby small calcium phosphate particles are formed proximal to said substrate; and
   means for holding and changing the position of said substrate in said trough to the direction of flow.

2. An apparatus according to claim 1, further comprising means for filtering particulate matter upstream from said distribution tank.

3. An apparatus according to claim 1, further comprising a sump in said coating trough, wherein said heating means is located in said sump.

4. An apparatus according to claim 1, wherein said changing means is a rocking means.

* * * * *